United States Patent [19]

Ransford

[11] Patent Number: 5,030,778
[45] Date of Patent: Jul. 9, 1991

[54] DECABROMODIPHENYL ALKANE PROCESS

[75] Inventor: George H. Ransford, Magnolia, Ark.
[73] Assignee: Ethyl Corporation, Richmond, Va.
[21] Appl. No.: 532,800
[22] Filed: Jun. 4, 1990
[51] Int. Cl.$^5$ .............................................. C07C 17/12
[52] U.S. Cl. ..................................... 570/208; 570/206
[58] Field of Search ................ 570/206, 208, 210, 211

[56] References Cited

U.S. PATENT DOCUMENTS

| | | | |
|---|---|---|---|
| 3,029,295 | 4/1962 | Thermet et al. | 570/206 |
| 3,752,856 | 8/1973 | Nacy et al. | 570/206 |
| 3,763,248 | 10/1973 | Mitchell | 570/206 |
| 3,833,674 | 9/1974 | Brackenridge | 570/206 |

FOREIGN PATENT DOCUMENTS 1411524  10/1975  United Kingdom ................ 570/206

OTHER PUBLICATIONS

Chemical Abstract 97, 38651d.
Chemical Abstract 46, 7084g.

Primary Examiner—Werren B. Lone
Attorney, Agent, or Firm—Edgar E. Spielman, Jr.

[57] ABSTRACT

This invention relates to a process for producing a product which is predominant in decabromodiphenyl alkane.

6 Claims, No Drawings

DECABROMODIPHENYL ALKANE PROCESS

BACKGROUND OF THE INVENTION

This invention relates to a process for preparing a product predominant in decabromodiphenyl alkane.

Polybromodiphenyl alkanes, e.g. decabromodiphenyl ethane, are known flame retardants for use in polyolefin- and in polystyrenic-based formulations. Generally, these flame retardants can be produced by the reaction of a diphenylalkane and bromine in the presence of a bromination catalyst. The reaction product will be a mixture of various diphenylalkane bromohomologs and will have an average bromine number which is equal to the average number of ar-substituted bromine atoms per molecule of brominated diphenylalkane in the product.

For several applications, a preferred product is one which has a very high decabromodiphenyl alkane content.

It is therefore an object of this invention to provide an economic and practical process for the production of a product which is at least 95 weight percent decabromodiphenyl alkane.

THE INVENTION

In accordance with this invention, decabromodiphenyl alkane is produced by a process which comprises: charging a reaction vessel with a bromination catalyst and liquid elemental bromine ($Br_2$); feeding liquid diphenylalkane to the reaction vessel at a point which is beneath the level of the charged liquid bromine, the liquid diphenylalkane being fed in an amount which provides from about 0.055 to about 0.033 moles of diphenylalkane per mole of elemental bromine initially charged; and maintaining the reaction mass at a temperature within the range of from about 30° C. to about 80° C. during the liquid diphenylalkane feed.

The diphenylalkane can be represented by the formula:

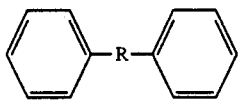

wherein R is an alkylene group containing 1 to 10 carbon atoms. Preferred R groups are methylene and ethylene which give, respectively, the preferred reactants, diphenylmethane and 1,2-diphenylethane. Exemplary of other diphenylalkanes are: 1-methyl-1,2-diphenylethane, 2,2-diphenylpropane 1,4-diphenylbutane, 1,6-diphenylhexane, 2,3-dimethyl-1,4-diphenylbutane, 2-ethyl-3-methyl-1,4diphenylbutane, 2-methyl-1,7-diphenylhexane, 1,9-diphenylnonane and 1,10-diphenyldecane. The diphenylalkane can be produced by various routes. For example, CA 97 38651d (Japanese Kokai 82/45114) and CA 46 7084g disclose the reaction of benzene and ethylene dihalide in the presence of aluminum trichloride to yield diphenylalkane. Another process for producing diphenylalkane includes the oxidative dimerization of toluene at a temperature of at least 400° C. in the presence of a metal oxide catalyst to yield diphenylethane and diphenylalkene. The latter product is then hydrogenated to remove the olefinic unsaturation.

It is not uncommon for the diphenylalkane reactant to be accompanied by various impurities. These impurities often give the final decabromodiphenyl alkane product an off color. Exemplary of these color-causing impurities is diphenylmethane. Diminishing the impurity content can be accomplished in a conventional manner, for example, the diphenylalkane can be recrystallized. See Example III wherein a recrystallization method is described.

The diphenylalkane is fed to the reaction vessel as a liquid, i.e. in the molten state or as a solute. In the molten state, the diphenylalkane is fed at a temperature above its melting point, but not at a temperature which is so high that the diphenylalkane experiences degradation. For diphenylethane, the melting point is about 53° C. to 55° C. and, hence, diphenylethane is preferably fed at a temperature of from about 55° C. to about 80° C. The higher temperatures are preferred as the viscosity of the molten diphenylethane can be lower thus making its feed to the reaction vessel more convenient. Most preferred is a temperature within the range of from about 70° C. to about 80° C.

It is preferred that the molten diphenylalkane be blanketed by a non-oxidizing atmosphere until it is fed into the reaction vessel. Such an atmosphere can be provided by most inert gases. For example, nitrogen, argon, neon, helium, krypton, xenon, and the like. By providing the inert atmosphere, it has been found that the color characteristics of the product are benefited. It is theorized that this color benefit is a result of preventing or reducing the production of oxidation decomposition impurities in the molten diphenylalkane feed. The decomposition impurities are probably 1-hydroxy-1,2-diphenylethane, benzaldehydes, benzyl alcohols and the like.

When fed as a solute, the diphenylalkane is in solution with a solvent, such as, a halogenated alkane or bromine. Exemplary halogenated alkanes are methylene bromide, methylene chloride, ethylene dibromide, ethylene dichloride, chloroform, bromoform, carbontetrachloride and the like. If the solvent is bromine, the bromine used can be counted toward the total amount of bromine used by the process. The most preferred solvents are methylene bromide, methylene chloride, ethylene dibromide and ethylene dichloride. Most preferred is methylene bromide.

The addition of the liquid diphenylalkane to the reaction vessel below the liquid level of the bromine is an important feature of the subject process. It has been found that with this sub-surface feed, a reaction product having a high average bromine number is obtained more quickly than is the case when the liquid bromine is fed above the liquid surface of the bromine. The depth below the liquid bromine surface at which the feed is to occur is that depth which is sufficient to diminish or obviate splattering of the reaction mass as the feed is occurring. Generally, a depth of from about 0.5 to about 1.0 inches, for laboratory scale equipment, and from about 6 inches to about 6 feet, for commercial scale equipment is suitable. In almost all cases, a depth of about one-half inch will be functional.

It is preferred that the bromine utilized in the process of this invention be essentially anhydrous, i.e. contain less than 50 ppm water, and contain no more than 10 ppm organic impurities, e.g. oil, grease, carbonyl containing hydrocarbons, iron and the like. With such a bromine purity, there is little, if any, impact on the color attributes of the diphenylalkane product. Available, commercial grade bromine may have such a purity. If, however, such is not available, the organic impurities and water content of the bromine can be conveniently reduced by mixing together a 3 to 1 volume ratio of bromine and concentrated (94-98 percent) sulfuric acid. A two phase mix is formed which is stirred for 10-16 hours. After stirring and settling, the sulfuric acid phase, along with the impurities and water, is separated from the bromine phase. To further enhance the purity of the bromine, the recovered bromine phase can be subjected to distillation.

The bromination catalyst used in the process of this invention is preferably $AlCl_3$ and/or $AlBr_3$, although use may be made of aluminum powder, iron powder, $FeCl_3$ and $FeBr_3$, alone or in combination with the aluminum trihalide(s). Other bromination catalysts are suitable provided that they have sufficient catalytic activity to provide for the extent of bromination called for under the process conditions which will be encountered. Catalytic quantities are used. Typically, the catalysts will be present in an amount within the range of about 0.1 to about 20 weight percent, based on the weight of the diphenylalkane reactant used in the process. A preferred amount is within the range of from about 6 to about 15 weight percent on the same basis, with from about 9.0 to about 11.0 weight percent being most preferred.

The bromination catalyst and bromine can be charged to the reaction vessel in any order or together. It is preferred that both be warmed prior to their charging so that they will form a mix which is at least near the temperature at which the reaction mass will be maintained during the diphenylalkane addition. While the foregoing is a preferred technique, it is possible, though maybe not as convenient, for the catalyst and bromine, prior to charging, to be at temperatures other than the diphenylalkane addition temperature. If, prior to charging, the catalyst and bromine temperatures are above the addition temperature, the temperature of the resultant mix in the reaction vessel can be lowered to obtain the desired addition temperature. However, care should be taken not to aspirate atmospheric moisture into the reaction vessel during such lowering. The presence of moisture in the reaction vessel is detrimental as many bromination catalysts are deactivated by contact with water.

The amount of elemental bromine ($Br_2$) charged to the reaction vessel should provide sufficient bromine to effect the degree of bromination sought and to provide an easily stirred reaction mass. After the reaction is complete, the bromine not used in the ar-substitution will be a liquid component of the reaction mass and will continue to serve the before-mentioned purpose of providing a stirrable reaction mass.

The diphenylalkane addition generally occurs over a period of time which is dependent upon the scale of the reaction, the ability to control the reaction temperature and the ability to handle hydrogen bromide evolution. On a laboratory scale, the addition typically requires from about 0.5 to about 1.5 hours while on a commercial scale, the addition could involve from about 1.0 to about 10.0 hours or longer. Four to five hours would be typical for the commercial scale.

Generally, the amount of diphenylalkane fed to the reaction vessel will provide from about 0.055 to about 0.033 moles of diphenylalkane per mole of bromine initially charged. Preferably, from about 0.05 to about 0.35 moles of diphenylalkane will be fed per mole of bromine initially charged. The most preferred amount is in the range of from about 0.043 to about 0.037 moles of diphenylalkane per mole of bromine.

During the diphenylalkane feed, the reaction mass temperature is kept within the range of from about 30° C. to about 80° C., and preferably within the range of from 50° C. to about 60° C. Since the bromination of diphenylalkane is exothermic, cooling of the reaction mass may be needed to obtain the addition temperature chosen. The heat of reaction can be removed from the reaction mass by cooling the reaction vessel or by having the reaction mass under reflux conditions so that heat can be removed by the use of an overhead condenser. When the diphenylalkane is fed as a molten material, the temperature of the reaction mass is preferably at least 45° C. and most preferably above the melting point of the diphenylalkane. Lower temperatures can be used, however, care must be taken to prevent freeze-up of the molten feed in the dip tube which is in contact with the relatively cool reaction mass. One technique that can be used when the reaction mass temperature is low is to feed the molten diphenylalkane at a high rate so that its residence time in the dip tube is very short.

It is preferred that the pressure in the reaction vessel be that which provides a refluxing condition at the selected reaction mass temperature. With a refluxing condition, control of the reaction mass temperature is facilitated. If temperature control is effected otherwise, i.e. by the use of heating or cooling jackets, etc. then the pressure can be any which is not prohibitive of the obtainment of the various defined parameters of the process. Also since temperatures above the boiling point of bromine are useful in the process of this invention, super atmospheric pressures, e.g. 5 psig can be used to obtain same.

The process of this invention is unique in that, after the diphenylalkane feed is at least substantially completed, no further maintenance of the formed reaction mass is generally needed to obtain a reaction product containing at least 95 weight percent decabromodiphenylalkane. Thus, product recovery can occur immediately after the diphenyalkane feed. In a preferred mode, product recovery can be initiated within one hour of the completion of the diphenylalkane feed. This one hour period is a useful process parameter as it allows for the cooling of the reaction mass and for preparation of the recovery step. It is to be understood that the practitioner can wait longer to recover the product as no harm is done except that process efficiency is compromised. If a maintenance period should ever be needed to obtain a certain purity of decabromodiphenyl alkane, then that maintenance period will be relatively short, e.g. one hour, as compared against the four to five hours used when the diphenylalkane feed is made above the liquid bromine surface. When the short maintenance period is used, the reaction mass, during the maintenance period, should be at a temperature within the range of from about 30° C. to about 80° C., and preferably 40° C. to about 60° C.

Since ar-bromination is a substitution reaction, HBr will be evolved so long as bromination is occurring. Hence, the evolution of HBr from the reaction mass can be used as an indicator to determine when a substantially ar-perbrominated reaction product has been obtained. The practitioner need only monitor the reaction for the cessation of HBr production and its evolution from the reaction mass. Once cessation or at least substantial cessation of HBr evolution is confirmed, recovery of the reaction product can be started.

After the reaction has at least substantially ceased, the reaction mass will comprise a liquid-solid mixture. The solid comprises brominated diphenylalkane, catalyst, entrained bromine and other impurities. The liquid will comprise mostly bromine. The recovery of the brominated diphenylalkane product and its entrained bromine is effected conventionally. A first step is to deactivate the catalyst. Deactivation can be accomplished by introducing water to the reaction mass. Steam is a preferred water form as its introduction to the reaction mass is bifunctional, i.e., the steams acts to steam strip nonentrained bromine from the reaction mass and to deactivate the catalyst The introduction of the water preferably occurs after the bromination activity has slowed or ceased. Another apparent advantage of the process of this invention is that the product produced does not tend to aggregate and froth during the steam strip.

After the steam strip, the remaining solids, which are at least about 95 weight percent decabromodiphenyl alkane, are first washed with an aqueous base, e.g. an aqueous solution of NaOH or $Na_2CO_3$, to neutralize and remove any HBr present, and then are water-washed. The product is of good color and can be further color treated to have superior color. A preferred product is one which contains 97 weight percent, and most preferably 99 weight percent, decabromodiphenyl alkane.

The color treatment will generally include the removal of entrained bromine from the product. This removal can be effected by oven-aging the product at a temperature within the range of from about 230° C. to about 250° C. for 6 to 20 hours. Another method comprises heating the product to a temperature above about 70° C. and subsequently fracturing the hot product particles thereby releasing any entrained bromine therefrom. The fracturing can be accomplished by grinding, impacting, etc. the product particles.

The decabromodiphenyl alkane predominant product of this invention may be used as a flame retardant in formulation with virtually any flammable material. The material may be macromolecular, for example, a cellulosic material or a polymer. Illustrative polymers are: olefin polymers, cross-linked and otherwise, for example, homopolymers of ethylene, propylene, and butylene; copolymers of two or more of such alkylene monomers and copolymers of one or more of such alkylene monomers and any other copolymerizable monomers, for example, ethylene/propylene copolymers, ethylene/ethyl acrylate copolymers and ethylene/vinyl acetate copolymers; polymers of olefinically unsaturated monomers, for example, polystyrene, e.g. high impact polystyrene, and styrene copolymers; polyurethanes; polyamides; polyimides; polycarbonates; polyethers; acrylic resins; polyesters, especially poly(ethyleneterephthalate) and poly(butyleneterephthalate); epoxy resins; alkyls; phenolics; elastomers, for example, butadiene/styrene copolymers and butadiene/acrylonitrile copolymers; terpolymers of acrylonitrile, butadiene and styrene; natural rubber; butyl rubber; and polysiloxanes. The polymer may also be a blend of various polymers. Further, the polymer may be, where appropriate, cross-linked by chemical means or by irradiation.

The amount of product used in a formulation will be that quantity needed to obtain the flame retardancy sought. It will be apparent to the practitioner that for all cases no single precise value for the proportion of the product in the formulation can be given since this proportion will vary with the particular flammable material, the presence of other additives and the degree of flame retardancy sought in any given application. Further, the proportion necessary to achieve a given flame retardancy in a particular formulation will depend upon the shape of the article into which the formulation is to be made, for example, electrical insulation, tubing and film will each behave differently. In general, however, the formulation may contain from about 5 to about 40 wt. percent, preferably 10 to 30 weight percent, of the product when it is the only flame retardant compound in the formulation.

It is especially advantageous to use the product with an inorganic compound, especially ferric oxide, zinc oxide, zinc borate, the oxide of a Group V element, for example, bismuth, arsenic, phosphorus and especially antimony, in the formulation. Of these compounds, antimony oxide is especially preferred. If such a compound is present in the formulation, the quantity of product needed to achieve a given flame-retardancy is accordingly reduced. Generally, the product and the inorganic compound are in a weight ratio of from about 1:1 to about 7:1, and preferably of from about 2:1 to about 4:1.

Formulations containing a flame retardant system comprised of the product of this invention and the above inorganic compounds may contain up to about 40 percent by weight of the system and preferably between 20 percent and 30 percent by weight.

Any of the additives usually present in formulations, e.g. plasticizers, antioxidants, fillers, pigments, UV stabilizers, etc. can be used in formulation with the product of this invention.

Thermoplastic articles formed from formulations containing a thermoplastic polymer and a product of this invention can be produced conventionally, e.g. by injection molding, extrusion molding, compression molding, and the like.

The following Examples merely illustrate the invention described herein and are not to be taken as limiting such inventions.

EXAMPLE I

A one-liter round-bottom flask was equipped with a mechanical stirrer, a thermometer, an addition funnel heated with a heat gun and a dip tube extending therefrom, a heating mantle and a reflux condenser vented to a water scrubber in line with a dry ice condenser. The addition funnel was charged with ground diphenylethane (50.0 g, 0.27 moles), and heated slowly with the heat gun. The flask was charged with bromine (1100.0 g, 6.85 moles) and catalyst ($AlCl_3$, 5.8 g). The level of the liquid bromine in the flask covered the end of the dip tube by about ¾ inch. Molten diphenylethane (kept at 55°–66° C.) was then added, through the dip tube, beneath the surface of the bromine over a period of about 2 hours. During the addition, the flask temperature was kept between 53° C. and 58° C. After the addition was complete, the reaction mixture was allowed to cool to 40° C. over about a 30 minute period. Water (100 mL) was then added dropwise to the flask followed by an additional 200 mL water addition. The bromine was distilled off to a vaporhead temperature of 100° C. To the remaining mass was added 125 mL $H_2O$ and 90 mL 25 percent aqueous NaOH. The resultant slurry was centrifuged and the recovered solids were washed with deionized water until neutral. The washed solids were dried at 110° C. for 2 hours and then oven aged at 210° C. for 7.5 hours. The overall yield was 254.1 g (95.1%). The product, by gas chromatography (G.C.) had a 98.2 area percent for decabromodiphenyl ethane.

EXAMPLE II

The procedure of Example I was repeated except that 7.8 g of AlCl$_3$ was used, the flask temperature was kept between 40° C. and 55° C. during most of the diphenylethane addition, and, after the diphenylethane addition, the flask contents were maintained at about 50° C. for about 5 hours. Also, the diphenylethane was not fed sub-surface of the bromine but rather was fed into the flask above the surface of the bromine. At the end of the diphenylethane addition period, G.C. analysis gave 88.2 area percent decabromodiphenyl ethane while at the end of the 50° C. maintenance period G.C. analysis gave 88.3 area percent decabromodiphenyl ethane.

EXAMPLE III

The following example illustrates a method for purifying diphenylethane.

A 1-L beaker was charged with methanol (300 mL). Crude diphenylethane (300 g) was then added. The contents of the beaker were heated and stirred at 65° C., and the resulting clear solution was then allowed to cool slowly to room temperature. A crystalline solid was formed. The solid was filtered and washed once with 120 mL methanol and then dried. The recovery was 274.5 g (91.5%). The recrystallized material had a melting point of 50° C.-54° C. which is slightly higher than the 49° C.-50° C. for the original starting diphenylethane. The starting diphenylethane had a Y.I. of 33.2 (L=81.2, a=−2.9, b=16.1) while the recrystallized diphenylethane material had a Y.I. of 2.8. (L=90.8, a=−0.4, b=1.4).

What is claimed:

1. A process for preparing a decabromodiphenyl alkane, which process comprises:
   (a) charging a reaction vessel with a bromination catalyst and liquid elemental bromine;
   (b) feeding liquid diphenylalkane to the reaction vessel at a point which is beneath the level of the charged liquid bromine, the liquid diphenylalkane being fed in an amount which provides from about 0.055 to about 0.033 moles of diphenylalkane per mole of elemental bromine initially charged; and
   (c) maintaining the reaction mass at a temperature within the range of from about 30° C. to about 80° C. during the liquid diphenylalkane feed.

2. The process of claim 1 wherein the diphenylalkane is diphenylethane.

3. The process of claim 1 wherein the liquid diphenylalkane is fed in an amount which provides from about 0.05 to about 0.35 moles of diphenylalkane per mole of bromine.

4. The process of claim 1 wherein the reaction mass is maintained at a temperature in the range of from about 50° C. to about 60° C. during the liquid diphenylalkane feed.

5. The process of claim 1 wherein water is added to the reaction mass to deactivate the bromination catalyst, the water addition being effected within one hour of the at least substantial completion of the liquid diphenylalkane feed.

6. The process of claim 1 wherein the liquid diphenylalkane is fed at a point which is about one-half inch below the level of the charged liquid bromine.

* * * * *